(12) United States Patent
Kleiman et al.

(10) Patent No.: US 6,287,579 B1
(45) Date of Patent: Sep. 11, 2001

(54) OXIDATIVELY STABLE LONG-CHAIN ETHYL ESTER EMOLLIENTS

(75) Inventors: Robert Kleiman, Mesa; Sambasivarao Koritala; Demetrios James G. Arquette, both of Tempe, all of AZ (US)

(73) Assignee: International Flora Technologies, Ltd (*) Notice: Subject to any disclaimer, the term of this patent is extended or adjusted under 35 U.S.C. 154(b) by 0 days.

(21) Appl. No.: 09/329,882

(22) Filed: Jun. 11, 1999

(51) Int. Cl.$^7$ ............... A61K 35/78; A61K 7/00
(52) U.S. Cl. ............. 424/401; 424/725; 424/764; 424/776
(58) Field of Search ................ 424/195.1, 401, 424/725, 764, 776

(56) References Cited

U.S. PATENT DOCUMENTS

| | | |
|---|---|---|
| 5,362,482 * | 11/1994 | Yoneyama et al. . |
| 5,552,167 | 9/1996 | Taylor et al. . |
| 5,560,917 * | 10/1996 | Cohen et al. . |
| 5,637,293 * | 6/1997 | Honda . |
| 5,876,736 | 3/1999 | Cohen et al. . |
| 5,902,590 | 5/1999 | Thomas et al. . |

FOREIGN PATENT DOCUMENTS

| | | |
|---|---|---|
| 40 05 819 A1 | 8/1991 | (DE) . |
| 40 23 593 A1 | 1/1992 | (DE) . |
| 06345617 * | 12/1994 | (JP) . |

OTHER PUBLICATIONS

"Preservatives: Antioxidants The Ultimate Answer to Oxidation", *Food Technology*, 40, 94–97, 100–102, (Sep. 1986).

* cited by examiner

Primary Examiner—Francisco Prats
Assistant Examiner—Susan D. Coe
(74) Attorney, Agent, or Firm—The Halvorson Law Firm

(57) ABSTRACT

Compositions or fluids comprising esters of long-chain organic molecules derived from natural oils, particularly plant, bean, seed and nut oils can be provided with increased oxygen stability by their combination with mixtures of particular classes of antioxidants, particularly combinations of at least one tocopherol and a supplemental ingredient selected from the class consisting of kojic acid, malic acid and ascorbic acid. The stabilization combination is particularly effective in combination with esters of long-chain organic molecules having less than 20% methylene interrupted polyunsaturation. An emollient composition is described that comprises a long-chain ethyl ester in combination with an oxidation stabilizing systems comprising at least one tocopherol and at least one supplemental additive selected from the group consisting of kojic acid, malic acid, and ascorbic acid. The long-chain ethyl ester may comprise an ethyl ester of a natural oil. The long-chain ethyl ester may have a percent methylene interrupted unsaturation of less than 20%, less than 15%, less than 10%, or less than 5%. The emollient composition may have the at least one supplemental additive present in an amount of from 0.01 to 2% or more by weight of said long-chain ethyl ester and the tocopherol is present in an amount of from 0.01 to 5% by weight of said long-chain ethyl ester. The emollient composition preferably has the long-chain ethyl ester selected from the class consisting of ethyl ester of macadamia oil, ethyl ester of hybrid sunflower, ethyl ester of babassu oil and meadowfoam having a percentage methylene interrupted unsaturation of less than 5.

7 Claims, No Drawings

OXIDATIVELY STABLE LONG-CHAIN ETHYL ESTER EMOLLIENTS

BACKGROUND OF THE INVENTION

1. Field of the Invention

The present invention relates to emollients, particularly emollients used in conjunction with cosmetic products (also referred to as cosmeceuticals) and pharmaceutical products that are externally applied to patients. The present invention particularly relates to the provision of oxidatively stable emollients derived from natural ingredients that provide a dry feel to the skin.

2. Background of the Art

Emollients are materials that are applied to the skin of subjects to produce softness or smoothness. They have been used for centuries in both cosmetic and pharmaceutical products. The original emollients were extracts or directly concentrated materials from plants or animals, while modern emollients also include partially synthetic (derivatives of natural products) or completely synthetic materials. The natural emollients, for the most part, have tended to provide a wet or oily feel and appearance to the skin of humans. The synthetic and partially synthetic emollients have been tailored to provide the specific type of appearance and feel desired in an end product. Even with this tailoring, there are only a few synthetic emollients that provide a highly satisfactory dry feel. Silicone emollients are the most successful dry-feel emollient.

In recent years there has been an increasing attempt in many commercial fields to use natural products from renewable sources or at least naturally derived products to both conserve resources and to reduce the pollution of the environment by materials that are not biodegradable. Silicones tend to be a class of synthetic material that are not easily degraded by the environment. The trend towards the use of natural products in cosmetics also provides motivation for manufacturers and compounders to seek alternatives to even the more successful synthetic components of their products, including silicone emollients.

In addition to the feel of an emollient, cosmetics and their ingredients must exhibit stability, both in storage and in use. The cosmetics must not deteriorate or separate in storage and use, and the individual ingredients should not decompose or otherwise undergo chemical changes that alter their desirable properties. One of the more common susceptibilities of products or components to ambient damage is from oxidation, and natural materials are clearly susceptible to oxidation, as can be commonly seen by the browning of fruit exposed to the air or the rancid smell of vegetable oils. Many foods, food additives, cosmetics, fragrances, medicaments, and colorants are well known to be subject to damaging effects from oxidation.

The most frequent means of reducing the effects of oxidation (including light amplified or stimulated oxidation) include oxygen excluding packaging (e.g., bottles, cans, oxygen impermeable polymer wraps, etc.), chemical modification of the ingredient to reduce its tendency towards oxidation while minimally altering its objective properties, and addition of antioxidants (e.g., reducing agents) to directly remove oxidative species before they oxidize the ingredient. Packaging controls are most effective where a product is to be used once, such as when a container is opened and air is introduced into the container. In this case the packaging does not provide complete protection against contact with oxygen. Chemical modification of an ingredient offers more general protection, assuming that a modification can be devised that both substantially reduces the tendency towards oxidation and also maintains the properties desired in the selection of the underlying chemical for a functional purpose, but can be an exhaustive task with no guarantees of success. The use of antioxidants offers a general approach to the problem for a wide variety of materials and fields, including even the protection of edible materials against premature oxidation. The use of antioxidants would appear to some to require little more than the appropriate selection of an antioxidant sold commercially for specific purposes to achieve a commercially viable product with a necessary level of oxidation resistance. However, antioxidants may have, and often display, unique interactions with ingredients on either a physical level (by not blending with the ingredients), on a chemical level by reacting with ingredients, or both. It is therefore necessary with some compositions, which require antioxidant protection for extensive research with no assurance of success. There are also such a wide variety of classes of antioxidants and so many variants within the classes that a search for an appropriate antioxidant is a highly problematic search, and the desire for the best antioxidant assures a time consuming process.

Among the more common classes of antioxidants are free-radical terminators, particularly those with available hydrogens from phenolic hydroxyl groups. Within that single class are the subclasses of butylated hydroxyanisole (BHA) and butylated hydroxytoluene (BHT), hydroquinones (such as tertiary-butylhydroquinones, propyl gallate, and tocopherols). Reducing agents, or oxygen scavengers, encompass another class of antioxidants and include ascorbic acid (vitamin C) and its derivatives (such as esters of ascorbic acid, ascorbyl esters such as ascorbyl palmitate); sulfites (such as sulfur sulfite, alkali metal sulfites, and bisulfites, including alkali metal bisulfites); glucose oxidase (including catalase); erythorbic acid and its derivatives. Chelating agents comprise another class of materials that have been used to address problems with oxidation and include citric acid and its derivatives, polyphosphates, and aminopolycarboxylic acids (such as ethylenediaminetetraacetic acid (EDTA)). There are additional antioxidant classes with less general areas of use.

U.S. Pat. No. 5,552,167, issued Sep. 3, 1996, describes a rice bran oil antioxidant, wherein high linolenic edible oils such as soybean oil and canola are stabilized by blending the oils with rice bran oil in amounts effective to render the oils stable to oxidation. Preferred embodiments employ from about 0.5% to about 10%, more narrowly from about 2% to about 5%, by weight rice bran oil specially processed to retain unsaponifiable matter. In one embodiment, physically refined rice bran oil is used. The natural stabilized oil is especially useful as a spray oil for crackers, nuts, chips, and other snack products.

U.S. Pat. No 5,876,736, issued Mar. 2, 1999, describes a cosmetic makeup composition containing at least one liposome-encapsulated or phospholipid-encapsulated moisturizer or re-hydrating agent and, preferably, an encapsulated blend of moisturizing/re-hydrating ingredients. For example, the encapsulated moisturizer or re-hydrating agent may be D,L-panthenol, D-panthenol, vitamin A palmitate, vitamin E acetate, methylsilanetriol mannuronate, natural oils such as tallow oil, macadamia nut oil, borage oil, evening primrose oil, kukui nut oil, rice bran oil, tea tree oil, a medium chain fatty acid ester of glycerol, such as glycerol triheptanoate, glyceryl trioctanoate, mineral water, silicones, and silicone derivatives. Mixtures of two or more of these ingredients may be used. A preferred moisturizer is a liposome vesicle containing D-panthenol.

U.S. Pat. No. 5,902,590, issued May 11, 1999, describes cosmetic and/or pharmaceutical formulations with increased viscosity and improved stability in storage which are distinguished by a content of selected esters of oligoglycerols with fatty acids as emulsifiers. This reference asserts that emulsifiers are required for the permanent homogeneous mixing of substances that would otherwise be immiscible with one another. Esters of fatty acids with polyhydric alcohols, for example pentaerythritol, dipentaerythritol, or self-condensation products of glycerol, so-called technical oligoglycerol mixtures, are often used for this purpose in cosmetic and pharmaceutical formulations, for example for the production of cremes and notions. A review of this subject by G. Schuster and H. Pospischil was published in Arztl. Kosmetol., 11, 30–37 (1981).

The use of polyglycerol esters as o/w emulsifiers for cosmetic formulations is described, for example, in J. Soc. Cosmet. Chem. 28, 733–740 (1977) and in Fette, Seifen, Anstrichmittel 88, 101–106 (1986). In addition, the use of selected polyglycerol fatty acid esters as cosmetic emulsifiers is claimed in DE-A1 40 05 819 and in DE-A1 40 23 593 (BASF). However, in cases where the esters based on unsaturated or saturated fatty acids mentioned in these documents are used, it has been found that the resulting emulsions are not always sufficiently stable in storage and/or are low in viscosity, i.e. have a viscosity which is not sufficiently high, so that problem-free dosing is difficult. The invention of that reference relates to cosmetic and/or pharmaceutical formulations that are characterized in that they contain statistical monoesters of technical triglycerol with saturated $C_{16}$–$C_{18}$ fatty acids as emulsifiers, the monoester content being from 30 to 50% by weight. It was asserted that it was surprising that the degree of self-condensation of the oligoglycerols in conjunction with the nature of the fatty acid and the percentage content of monoesters has a critical bearing on the properties of the resulting emulsifiers. That invention includes in particular the observation that the establishment of a percentage monoester content of 30 to 50% in the emulsifiers according to the invention leads to a significant improvement in storability and viscosity compared with otherwise known products of the prior art.

SUMMARY OF THE INVENTION

Compositions or fluids comprising esters of long-chain organic molecules derived from natural oils, particularly plant, bean, seed and nut oils can be provided with increased oxygen stability by their combination with mixtures of particular classes of antioxidants, particularly combinations of at least one tocopherol and supplemental ingredient selected from the class consisting of kojic acid, malic acid and ascorbic acid. The stabilization combination is particularly effective in combination with esters of long-chain organic molecules having less than 20% methylene interrupted polyunsaturation.

An emollient composition is described that comprises a long-chain ethyl ester in combination with an oxidation stabilizing system comprising at least one tocopherol and at least one supplemental additive selected from the group consisting of kojic acid, malic acid, and ascorbic acid. The long-chain ethyl ester may comprise an ethyl ester of a natural oil. The long-chain ethyl ester may have a percent methylene interrupted unsaturation of less than 20%, less than 15%, less than 10%, or less than 5%. The emollient composition may have the at least one supplemental additive present in an amount of from 0.01 to 2% or more by weight of said long-chain ethyl ester and the tocopherol is present in an amount of from 0.01 to 5% by weight of said long-chain ethyl ester. The emollient composition preferably has the long-chain ethyl ester selected from the class consisting of ethyl ester of macadamia oil, ethyl ester of hybrid sunflower, ethyl ester of babassu oil and ethyl ester of meadowfoam oil having a percentage methylene interrupted unsaturation of less than 5.

DETAILED DESCRIPTION OF THE INVENTION

Ethyl esters of oils, particularly form triglyceride oils are commercially available from a number of different sources and are available from many different natural material sources. For example, the CTFA (Cosmetic Toiletry and Fragrance Association) lists at least the following ethyl esters of natural oils as commercially available: Kukui Nut (*Aleurites Molucunna*) oil ethyl ester; Borage seed oil (*Borago Officinalis*) ethyl ester; Hazelnut (*Corylus Avellana*) oil ethyl ester; Sweet Almond oil ethyl ester; Apricot kernel oil ethyl ester; the ethyl ester of arachidonic acid (5,8,11,14-Eicosatetraenoic acid ethyl ester); Avacado ethyl ester (ethyl perseate); ethyl esters of isostearic acid, lactic acid, lauric acid, myristic acid, stearic acid, palmitic acid (hexadecanoic acid), ricinoleic acid (12-hydroxy-9-octadecanoic acid) linoleic acid; Mink oil ethyl ester (ethyl mustelate); olive oil ethyl ester (ethyl olivoleate); ethyl ximenynate (ethyl santalbate); silybum marianum ethyl ester (derived from silybum Marianum oil); etc. Ethyl esters of commercially available oils or ethyl esters of oils that could be readily made by conventional reaction with ethanol as described herein also include macadamia nut oil ethyl ester; meadowfoam oil ethyl ester; Babassu oil ethyl ester; canola oil ethyl ester; Sesame oil ethyl ester; sunflower oil ethyl ester, wheat germ oil ethyl ester, ethyl esters of special hybrids of these oils (e.g., high-oleic safflower oil, hybrid sunflower oil), menhaden oil ethyl ester soybean oil ethyl ester; rapeseed oil ethyl ester and others. These ethyl esters can be readily manufactured by interesterification of the oils with ethyl alcohol (preferably anhydrous ethyl alcohol) and an esterification catalyst. Many of these oils are primarily indicated as skin-conditioning agents and/or emollients. The individual esters vary in their chemical characteristics, substituent groups, molecular weights, and degrees of unsaturation. The last mentioned characteristic, the degree of unsaturation has some particular significance on the selection of preferred materials in the practice of the present invention, with oils having less than 20% methylene interrupted polyunsaturation being generally more desirable, unsaturation of less than 15%, being particularly desirable, unsaturation levels of equal to or less than 12%, 8% and 5% (e.g., about 1–5%) being respectively more desirable.

These oils and esters of the oils have a high tendency towards oxidative degradation, with all of the esters (except for meadowfoam at 48) displaying an oxidative stability index (OSI, as outlined in The Official and Tentative Methods of the American Oil Chemists' Society, AOCS Method Cd 12b-92) of less than ten hours in the absence of protective antioxidant additives. The use of the most common antioxidants, e.g., BHA and BHT, to ethyl esters of these natural long-chain (e.g., from at least about 8 carbon atoms to 30 or more carbon atoms in the primary aliphatic chain) oils, fats or fatty materials (e.g., BHA and BHT, for example) tends to improve the stability of the oils that are already more stable, without providing dramatic improvements levels in OSI to oils that display the worst or poorest performance levels with regard to OSI in the absence of antioxidants. There is therefore a clear need for the ability to provide antioxidant protection to long-chain ethyl esters that are useful as emollients.

The present invention provides emollient compositions displaying improved oxidation resistance comprising ethyl esters of long-chain oils, fats, or fatty materials, at least one tocopherol and at least one supplemental additive selected from the group consisting of kojic acid, malic acid and ascorbic acid. The acids may be used in amounts of from about 0.01% by weight of the ethyl ester to about 2.5% by weight of the ethyl ester, depending upon the particular formulation, the ester used, and other additives in the composition. In general, relatively low amounts of the acids used in combination with the tocopherol (which may itself be used in amounts of from 0.01% to 5% by weight of the ethyl ester as, for example, from 0.04% to 2.0%, 0.05 to 1.5%, 0.04% to 1.0%, 0.05 to 0.5%, and 0.08 to 0.3% by weight of the acid component are highly effective. Malic acid is known in the cosmetic art as an alpha-hydroxy acid exfolient and kojic acid is known as a skin whitener, but their commercial uses in those capacities is generally understood in the art to utilize amounts of from about 3% to 10%, even if there may be some generic disclosure in the art for their use in broader ranges for those purposes. In the compositions of the present invention, each 0.1% concentration approximately translates to 1000 ppm in the final emollient only composition. The use of the combination additive system of the present invention has been shown to provide OSI values of over 200 hours for ethyl ester of macadamia oil (e.g., 234 hours) and as much as 140 OSI for high-oleic sunflower oil.

Additional Additives

In addition to the essential ingredients in the emollient compositions of the present invention, further materials may be present in the composition for functional or aesthetic reasons. Additional antioxidants from the classes described herein and/or antioxidants, including tocopherols (vitamin E), tocotrienols (compounds homologous to tocopherols that differ by the presence of three unsaturated bonds in the phytyl side chain), and oryzanol (a mixture of ferulic acid esters of sterols, e.g., beta-sitosteryl ferulate and methyl ferulate, and triterpene alcohols, e.g., 24-methylenecycloartenyl ferulate; see Bailey's Industrial Oil and Fat Products, 4th ed., John Wiley, New York, 1979, volume 1, pages 407 to 409) may be present. Fragrances, colorants (e.g., dyes or pigments), topically applied medications, UV absorbers, whitening agents, emulsifying agents, binder, scrubbing particulates and the like may be present.

Fatty elements in addition to the stabilized ethyl esters that may be used can be selected from mineral oils like paraffin or petroleum oils, silicone oils; vegetable oils like coconut, almond, apricot, corn, jojoba, olive, avocado, sesame, palm, eucalyptus, rosemary, lavender, pine, thyme, mint, cardamon, orange blossoms, soy beans, bran, rice, colza, and castor oils; animal oils and fats like tallow, lanolin, butter oil; fatty acid esters, fatty alcohol esters, and waxes whose melting point is the same as the skin's (e.g., animal waxes like bee's wax, carnauba or candelilla waxes, mineral waxes like microcrystalline waxes and synthetic waxes like polyethylene or silicone waxes). All acceptable oils used in cosmetology can be used, like the ones that have been mentioned in the CTFA's book, Cosmetic Ingredient Handbook, First edition, 1988, The Cosmetic, Toiletry and Fragrance Association, Inc., Washington.

Cosmetically or dermatologically active substances, meaning active cosmetics chosen from anti-acne agents, anti-microbial agents, anti-perspiration agents, astringents, deodorants, hair removers, external analgesics, hair conditioners, skin conditioners, sun protecters, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and mineral substances for synthetic coverings. These substances represent from 1 to 20% by weight of the composition.

Detergent or foaming agents may include, but are not limited to, disodic cocoamphodiacetate salts (MIANOL C2M of RHONE POULENC); lauroylether sulfosuccinate disodic salts (SETACIN 103 of ZSCHIMMER); the vegetable protein acylates (PROTEOL VS22 of SEPPIC); the cocoyl glutamate triethanolamine salts (acylglutamate CT12 d'AJINOMOTO); the lauroyl sarcosinate sodium salt (ORAMIX 130 of SEPPIC); the glucoside decyl-ether (ORAMIX NS10 of SEPPIC); the sodium sulfate lauroyl ethers (NEOPON LOS RO of WITCO).

Pasty active compounds like lanolin by-products (acetyl lanolin), lanolin, and lanolin alcohols; cholesterol by-products like cholesterol esters (12 cholesteryl hydroxy stearate); pentaerythritol hydroxylated esters (SALACOS 168M); linear mono-esters like butyl stearate, arachidyl propionate or stearyl heptanoate; and triglycerides with a fatty chain less than $C_{16}$ can also be used. These substances may be water-soluble, lipid-soluble, lipid-soluble and water-soluble at the same time, or dispersible. They can be chosen from the compounds that are in the Cosmetic Ingredient Handbook, at pages 51 to 101.

Surface active agents, such as cationic, anionic, non-ionic and/or Zwitterionic may be used. These surface agents can be chosen, for example, from the hydrophillic surface agents, like glycols, such as hexylene glycol, butylene-1,2 glycol, ethyl-2-hexyl sulfosuccinate; oxyethylene octylphenol, and the salts derived from cocoyl and lauroyl collagen, sorbitan palmitate, and the polyoxyethylene byproducts of sorbitol palmitate esters, and salts of fatty chain quaternary ammonium. Suitable anionic surfactants that may be used include the water-soluble alkali metal or ammonium salts having alkyl radicals containing from about 8 to about 22 carbon atoms, the term alkyl being used to include the alkyl portion of higher acyl radicals.

Examples of suitable synthetic anionic surfactants are sodium or ammonium alkyl sulfates, especially those obtained by sulfating higher ($C_8$–$C_{18}$) alcohols produced, for example, from tallow or coconut oil; alkyl ($C_9$–$C_{20}$) benzene sulfonates, particularly sodium linear secondary alkyl ($C_{10}$–$C_{15}$) benzene sulfonates; alkyl glyceryl ether sulfates, especially those ethers of the higher alcohols derived from tallow or coconut oil and synthetic alcohols derived from petroleum; coconut oil fatty monoglyceride sulfates and sulfonates; salts of sulfuric acid esters of higher ($C_8$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and potassium salts of fatty acid amides of methyl taurine; alkane mono-sulfonates such as those derived from reacting alpha-olefins ($C_8$–$C_{20}$) with sodium bisulfite and those derived from reacting paraffins with $SO_2$ and $Cl_2$ and then hydrolyzing with a base to produce a random sulfonate; and olefin sulfonates which term is used to describe the material made by reacting olefins, particularly $C_{10}$–$C_{20}$ alpha-olefins, with $SO_3$ and then neutralizing and hydrolyzing the reaction product. The preferred anionic surfactants are sodium or ammonium ($C_{10}$–$C_{18}$) alkyl sulfates and ($C_{10}$–$C_{18}$) alkyl polyethoxy (1–11 EO, ethylene oxide) sulfates and mixtures thereof having differing water solubilities.

Particularly preferred anionic surfactants comprise a mixture of a ($C_{10}$–$C_{18}$) alkyl sodium or ammonium sulfate or sulfonate or a ($C_{14}$–$C_{18}$) alpha-olefin sodium or ammonium sulfonate (AOS) and a ($C_8$–$C_{12}$) alkyl polyethoxy (2–4 EO) sodium or ammonium sulfate. Mixtures containing a major amount of the alkyl sulfates, olefin sulfonates or alkyl alkoxy sulfates with aryl sulfonates such as sodium cumene sulfonate, sodium xylene sulfonate and sodium benzene sulfonate are also optional.

The amount of anionic surfactant present in the composition will generally range from about 0 or 1% or 4 to 12% by weight (total ingredients) by weight. The amphoteric or Zwitterionic surfactants may optionally be present at a level of at least about 0.1 or at least about 0.25% by weight of the total composition.

Examples of amphoteric surfactants that may be used in the compositions of the present invention include betaines and compounds that can be broadly described as derivatives of aliphatic secondary and tertiary amines wherein the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isethionate, N-higher alkyl aspartic acids and the products sold under the trade name "Miranol".

Makeup or cosmetic compositions of the present invention also contain as an optional ingredient a film forming skin tightening agent, particularly a plant derived biological polysaccharide cosmetic ingredient that may be combined with a casein hydrolyzate. The polysaccharides that can be used in the practice of the present invention include, for example, lecithin, pectin, karaya gum, locust bean gum, xanthan gum and mixtures thereof. An especially preferred film forming skin tightening agent of the present invention is Pentacare™ HP, a commercially available blend of plant polysaccharides and hydrolyzed casein from Pentapharm LTD., Basel, Switzerland.

Suitable co-emulsifiers are both known w/o (water in oil) and o/w (oil in water) emulsifiers. Typical examples of fats are glycerides, while suitable waxes include inter alia beeswax, paraffin wax or microwaxes. Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose, also fatty alcohols, monoglycerides and fatty acids, polyacrylates, polyvinyl alcohol and polyvinyl pyrrolidone. In the context of the present invention, biogenic agents are, for example, plant extracts, protein hydrolyzates and vitamin complexes. Typical film formers are, for example, polyvinyl pyrrolidone, vinyl pyrrolidonelvinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearl esters are, for example, glycol distearic acid esters, such as ethylene glycol distearate, and also fatty acids and fatty acid monoglycol esters. The dyes used may be selected from any of the substances that are permitted and suitable for cosmetic purposes, as listed for example in the publication "Kosmetische Farbemittel" of the Farbstoffkommission der Deutschen, at pages 81–106. These dyes are typically used in concentrations of 0.001 to 0.1% by weight, based on the mixture as a whole.

The total percentage content of auxiliaries and additives may be 1 to 50% by weight and may be 5 to 40% by weight, based on the formulation. The formulations may be produced in known manner, i.e. for example by hot, cold, hot-hot/cold or PIT emulsification. These are purely mechanical processes and do not involve a chemical reaction. The cosmetic and/or pharmaceutical formulations may have a water content of 25 to 95% by weight and preferably 50 to 75% by weight.

EXAMPLES

The following non-limiting examples are provided for further enablement of the practice of the present invention and are not to be construed as specifically limiting the practice of the present invention in any way.

The compositions described in the following table were formulated and then subjected to the OSI test (outlined in The Official and Tentative Methods of the American Oil Chemists' Society, AOCS Method Cd 12b-92) and the results recorded.

TABLE

| Ethyl Ester of | No Additive | Tocopherols | Tocopherols + Kojic Acid | Tocopherols + Malic acid | Tocopherols + Asc. Acid | % Methylene Unsaturation |
|---|---|---|---|---|---|---|
| Macadamia | 4.5 | 49.5 | 86.0 | 88.8 | 234.4 | 3 |
| Hybrid Sunflower | 2.2 | 10.0 | 76.3 | 73.4 | 139.7 | 4 |
| Sesame | 4.7 | 6.0 | 8.1 | 12.9 | 44.6 | 44 |
| Babassu | 5.8 | 23.3 | 1387.1 | 122.6 | 162.8 | 2 |
| Meadowfoam | 48 | 103.2 | 125.1 | 169.1 | 265.7 | 1 |
| Canola | 3.4 | 6.4 | 8.3 | 10.5 | 42.3 | 28 |
| Mink | 3.0 | 6.6 | 21.1 | 21.3 | 117.4 | 15 |
| High-Oleic Safflower | 2.7 | 8.9 | 29.8 | 31.3 | 81.3 | 12 |
| Sweet Almond | I.7 | 5.2 | 11.25 | 13.5 | 39.8 | 25 |
| Milkweed | 1.3 | 1.8 | 4.6 | 6.9 | 7.4 | 51 |

All data in the Table (except for the Percent (%) Methylene Unsaturation) are OSI values. As can be seen from this data, the combined use of the tocopherol and at least one of the additional components selected from the group consisting of Kojic acid, malic acid and ascorbic acid produces improvement in the OSI results. The data clearly shows that significantly improved results are provided with oils having a percent methylene interrupted unsaturation equal to or less than 20% (that is, with oils having less than 20% methylene interrupted polyunsaturation being generally more desirable, methylene interrupted unsaturation of less than 15%, methylene interrupted unsaturation levels of equal to or less than 12%, 8% and 5% (e.g., about 0.5–5% or 1–5%) being respectively more desirable). It is to be noted that for all materials having a percentage methylene interrupted unsaturation of less than 20% (except for the inherently stable meadowfoam ethyl ester), the improvement in OSI stability was at least twenty-eight fold, while for materials having a percent methylene interrupted unsaturation of greater than 20%, the increase was between about 5–25 fold, with only Sweet Almond having an increase of over 15 fold, in part because of a very low OSI value without additives, even with a relatively low OSI value (39.8) even with the additives of the present invention.

Vegetable oils, such as soybean oil, are complex mixtures of triacylglycerols, esters of glycerols with three fatty acid chains per molecule. The term "percent methylene interrupted unsaturation" is used as a description of the internal structure of these various triacylglycerols. The term literally means the weight percent of acyl groups having double bonds separated by or interrupted by a methylene group, —$CH_2$—. This term is used to better explain the reactivity of air fatty acyl groups whose double bonds are so far away from one another that they behave chemically as monoenoic fatty acyl groups. For example, consider the double bonds at the delta-5 and delta-13 positions of meadowfoam oil. The double bonds are so remote from each other that the acyl group acts as if it were monoenoic. The two double bonds do not interact in a way that would cause the fatty acid group to behave as a dienoic molecule rather than as a monoenoic molecule. The weight percent of acyl groups having double bonds separated by a methylene group is calculated, then added to other such acyl groups to determine the total percent methylene interrupted unsaturation. Soybean oil, for example, has two such acyl groups, the linoleic and linolenic groups. The weight percentages of these two acyl groups in soybean oil is usually 52% and 6%, respectively. The percent methylene interrupted unsaturation is therefore 58%.

What is claimed is:

1. An emollient composition comprising
    a) a long-chain ethyl ester, wherein said long-chain ethyl ester is a long-chain ethyl ester having at least eight carbon atoms in the primary aliphatic chain, and said long-chain ethyl ester has a percent methylene interrupted unsaturation of less than 20%, in combination with
    b) at least one tocopherol and at least one supplemental additive selected from the group consisting of kojic acid, malic acid, and ascorbic acid, wherein said tocopherol is present in an amount of from 0.01 to 5% by weight of said long-chain ethyl ester, wherein said tocopherol and said at least one supplemental additive in combination provide a greater oxidation stability to the long-chain ethyl ester relative to the oxidation stability that each one provides individually and wherein
said long-chain ethyl ester is selected from the class consisting of ethyl ester of macadamia oil, ethyl ester of hybrid sunflower oil, ethyl ester of babassu oil and meadowfoam oil having a percentage methylene interrupted unsaturation of less than 5.

2. An emollient composition comprising
    a) a long-chain ethyl ester, wherein said long-chain ethyl ester is a long-chain ethyl ester having at least eight carbon atoms in the primary aliphatic chain, and said long-chain ethyl ester has a percent methylene interrupted unsaturation of less than 5%, in combination with
    b) at least one tocopherol and at least one supplemental additive selected from the group consisting of kojic acid, malic acid, and ascorbic acid, wherein said tocopherol and said at least one supplemental additive in combination provide a greater oxidation stability to the long-chain ethyl ester relative to the oxidation stability that each one provides individually and wherein, and
said long-chain ethyl ester is selected from the class consisting of ethyl ester of macadamia oil, ethyl ester of hybrid sunflower oil, ethyl ester of babassu oil and meadowfoam oil.

3. An emollient composition comprising
    a) a long-chain ethyl ester, wherein said long-chain ethyl ester is a long-chain ethyl ester having at least eight carbon atoms in the primary aliphatic chain, and said long-chain ethyl ester has a percent methylene interrupted unsaturation of less than 5%, in combination with
    b) at least one tocopherol and at least one supplemental additive selected from the group consisting of kojic acid, malic acid, and ascorbic acid,
wherein said tocopherol and said at least one supplemental additive in combination provide a greater oxidation stability to the long-chain ethyl ester relative to the oxidation stability that each one provides individually and wherein said long-chain ethyl ester is selected from the class consisting of ethyl ester of macadamia oil, ethyl ester of hybrid sunflower oil, ethyl ester of babassu oil and meadowfoam oil.

4. An emollient composition comprising
    a) Macadamia nut oil ethyl ester having a percent methylene interrupted unsaturation of less than 20% in combination with
    b) at least one tocopherol and at least one supplemental additive selected from the group consisting of Kojic acid, malic acid, and ascorbic acid,
wherein said tocopherol and said at least one supplemental additive in combination provide a greater oxidation stability to the Macadamia nut oil ethyl ester relative to the oxidation stability that each one provides individually.

5. The emollient composition of claim 4 wherein said supplement additive comprises ascorbic acid.

6. The emollient composition of claim 4 wherein said at least one supplemental additive is present in an amount of from 0.01 to 2% by weight of said macadamia nut oil ethyl ester.

7. The emollient composition of claim 6 wherein said Macadamia nut oil ethyl ester has a percent methylene interrupted unsaturation of less than 10%.

* * * * *